(12) United States Patent
Hasumi et al.

(10) Patent No.: US 7,655,393 B2
(45) Date of Patent: Feb. 2, 2010

(54) ADOPTIVE IMMUNE CELLS FOR TUMOR VACCINES

(75) Inventors: Kenichiro Hasumi, Tokyo (JP); Akira Imaizumi, Koganei (JP); Masamichi Iwama, Yokohama (JP); Mitsuaki Goto, Kawasaki (JP)

(73) Assignees: Shukokai Incorporated, Tokyo (JP); Celagix, Res. Ltd., Yokohama-shi, Kanagawa (JP)

( * ) Notice: Subject to any disclaimer, the term of this patent is extended or adjusted under 35 U.S.C. 154(b) by 191 days.

(21) Appl. No.: 11/579,280

(22) PCT Filed: May 11, 2004

(86) PCT No.: PCT/JP2004/006599

§ 371 (c)(1),
(2), (4) Date: Nov. 2, 2006

(87) PCT Pub. No.: WO2005/108554

PCT Pub. Date: Nov. 17, 2005

(65) Prior Publication Data

US 2007/0286847 A1      Dec. 13, 2007

(51) Int. Cl.
*A01N 1/02* (2006.01)

(52) U.S. Cl. ......................................................... 435/2

(58) Field of Classification Search ........................ None
See application file for complete search history.

(56) References Cited

U.S. PATENT DOCUMENTS

| 5,851,756 | A | * | 12/1998 | Steinman et al. | ............... | 435/2 |
| 6,121,044 | A | | 9/2000 | Peshwa et al. | | |
| 6,642,050 | B1 | * | 11/2003 | Goto et al. | .................. | 435/395 |
| 2006/0177420 | A1 | | 8/2006 | Felzmann | | |

FOREIGN PATENT DOCUMENTS

| JP | 05-041983 | A | 2/1993 |
| JP | 08-317786 | A | 12/1996 |
| JP | 2001-520509 | A | 10/2001 |
| JP | 2002-69001 | A | 3/2002 |
| WO | WO 97/03186 | A2 | 1/1997 |
| WO | WO 97/05239 | A1 | 2/1997 |
| WO | WO 2004/024900 | A1 | 3/2004 |

OTHER PUBLICATIONS

Hirose, et al, "Regulation of Asialoglycoprotein Receptor Expression in the Proliferative State of Hepatocytes," Biochemical and Biophysical Research Communications, 287 (2001) 675-681.
Ishida, et al, "Cell Adhesion Aside from Integrin System Can Abrogate Anoikis in Rat Liver Cells by Down-regulation of FasL Expression, not by Activation of PI-3K/Akt and ERK Signaling Pathway," Biochemical and Biophysical Research Communications, 300 (2003) 201-208.
Na, et al, "Conjugation of Arg-Gly-Asp (RGD) Sequence in Copolymer Bearing Sugar Moiety for Insulinoma Cell Line (MIN6) Culture," Biosci. Biotechnol. Biochem, 65 (6), 1284-1289, (2001).
English-language International Preliminary Report on Patentability dated Nov. 14, 2006 and Written Opinion of the International Searching Authority, of International Application PCT/JP2004/006599 filed May 11, 2004; Applicants: Shukokai Incorporated et al.
D. Choi et al, "Dendritic Cell-based Vaccines in the Setting of Peripheral Blood Stem Cell Transplantation: . . . ", *Clin. Cancer Res.*, vol. 4, pp. 2709-2716, Nov. 1998.
F.J. Hsu et al, "Vaccination of patients with B-cell lymphoma . . . ", *Nat. Med.*, vol. 2, No. 1, pp. 52-58, Jan. 1996.
M. Takamizawa et al, "Cellular and Molecular Basis of Human γδ T Cell Activation", *J. Clin Invest.*, vol. 95, pp. 296-303, Jan. 1995.
V.L. Reichardt et al, "Idiotype Vaccination Using Dendritic Cells After Autologous Peripheral Stell Cell Transplantation for Multiple Myeloma . . . ", *Blood*, Vo. 93, No. 7, pp. 2411-2419, Apr. 1999.
J. Wang et al, "Eliciting T Cell Immunity Against Poorly Immunogenic Tumors . . . ", *J. Immunol.*, vol. 161, pp. 5516-5524, 1998.
M.A. Morse et al, "A Phase I Study of Active Immunotherapy with Carcinoembryonic Antigen Peptide . . . ", *Clin. Cancer Res.*, vol. 5, pp. 1331-1338, Jun. 1999.
R.J. Hodes et al, "Cellular and genetic control of antibody responses in vitro", *Eur. J. Immunol.*, vol. 7, pp. 892-897, 1977.
Jos W.M Van Der Meer, "Culture of Mononuclear Phagocytes on a Teflon Surface to Prevent Adherence", *J. Exp. Med.*, vol. 147, pp. 271-276, 1978.
Jos W.M. Van Der Meer, "Suspension Cultures of Mononuclear Phagocytes in the Teflon Culture Bag", *Cell. Immunol.*, vol. 42, pp. 208-121, 1979.
R.M. Steinman et al, "Dendritic Cell Development and Maturation", *Adv. Exp. Med.*, pp. 1-6, 1997.

* cited by examiner

Primary Examiner—Misook Yu
(74) Attorney, Agent, or Firm—Frishauf, Holtz, Goodman & Chick, P.C.

(57) ABSTRACT

The present invention provides a method for preparing adoptive immune cells comprising the following steps of a) obtaining mammalian antigen-presenting associated cells; b) culturing the resulting cells in a culture vessel coated with a sugar chain-containing polymer; and c) detaching the cells by shaking the culture vessel without treating the cells with enzyme and without using a cell detaching tool; adoptive immune cells obtained by this preparing method; a culture vessel coated with a sugar chain-containing polymer for use in this preparation method; a kit for preparing an adoptive immune cell vaccine; and a method and a medicine for treating a malignant tumor, type I diabetes, atopic allergic diseases or infections using the adoptive immune cells.

39 Claims, 3 Drawing Sheets

ADOPTIVE IMMUNE CELLS FOR TUMOR VACCINES

This application is the United States national phase application of International Application PCT/JJ2004/006599 filed May 11, 2004.

TECHNICAL FIELD

The present invention relates to adoptive immune cells for tumor vaccines and the like.

BACKGROUND ART

Cell Immunotherapy for Cancer

The following methods are known as cell immunotherapy methods for the treatment of cancer (Choi D et al., Clin. Cancer Res., 4, 2709-2716, 1998, Hsu F J et al., Nat Med., 2, 52-58, 1996, Takamizawa M et al., J Clin. Invest 95, 296-303, 1995, Reichardt V L et al., Blood, 93, 2411-2419, 1999, wang J et al., J. Immunol., 161, 5516-5524, 1998, Morse M A et al., Clin. Cancer Res., 5, 1331-1338, 1999). Cells obtained by selectively collecting dendritic cells (DC)/macrophages by apheresis are further cultured in a culture liquid to which has been added interleukin 4, GMCSF and TNF-α to induce differentiation (Steinman R M et al., Adv. Exp. Med.1997). Subsequently, the cells are detached and recovered from the culture vessel by any method of (i) enzyme treatment, (ii) scraping with a scraper, or (iii) blowing the culture liquid with a pipette (Hodes R J and Singer A., Eur. J. Immunol., 7, 892-897, 1977). Mature DC/macrophages obtained in this manner are then co-cultured in medium containing a target antigen to produce cancer-specific antigen-presenting cells having a complex of target antigen epitope and MHC class II molecules. The antigen-presenting cells adhered to the bottom of the culture vessel are detached and recovered by any method of (i) enzyme treatment, (ii) scraping with a scraper, or (iii) blowing on the culture liquid with a pipette, followed by administering to the same person in the form of cancer-specific, antigen-presenting cells.

In conventional immune cell therapy, cultured cells were detached and recovered from a culture vessel by any method of (i) enzyme treatment, (ii) scraping with a scraper, or (iii) blowing on the culture liquid with a pipette (Hodes RJ and Singer A., Eur. J. Immunol., 7, 892-897, 1977).

Detachment and Recovery Methods Using Enzymes

A method using trypsin is most commonly used for detaching and recovering adhered cells (Hodes R J and Singer A., Eur J. Immunol., 7, 892-897, 1977). In this method, after washing the culture vessel to which the cells are adhered with PBS not containing $Ca^{++}$ or $Mg^{++}$, PBS containing 0.05% trypsin and 0.024% EDTA is added to a depth of 0.1 to 1 mm from the bottom of the flask and allowed to stand undisturbed at room temperature. 5 to 10 minutes later, culture liquid containing 0.1 to 1% albumin chilled to 4° C. is added followed by stirring gently to gather the suspended cells. The gathered cells are then washed with culture liquid containing albumin for use in subsequent experiments.

However, detaching methods using enzymes have a problem in that, since functional protein molecules on the cell membrane of the adhesive immune cells are digested and decomposed, even if they are detached and recovered, they are unable to adequately demonstrate cell functions. Although methods using a Teflon film and so forth for the culture vessel have been previously attempted (Van der Meer J W M, Bulterman D., Van Zwet T L, Elzenga-Claasen I, and Van Furth R, J. Exp. Med., 147, 271-276, 1978; Van der Meer J W M, Van de Gevel J S, Elzenga-Claasen I, and Van Furth R, J, Cell Immunol., 42, 208, 1979), since adhesion to the culturing surface is obstructed, it was difficult to acquire the function by culturing. Consequently, there is a need to develop a culture base having the offsetting properties of maintaining adhesion during culturing, but losing affinity for cells during detaching and recovery.

An object of the present invention is to provide adoptive immune cells capable of adequately demonstrating cell functions by using a culture base that solves the aforementioned problems.

DISCLOSURE OF THE INVENTION

As a result of conducting extensive research, the inventors of the present invention found that the aforementioned problems can be solved by using a culture vessel coated with a sugar chain-containing polymer typically represented by PVLA, thereby leading to completion of the present invention. Thus, the present invention provides the following.

1. A method for preparing adoptive immune cells comprising the following steps:
   a. obtaining mammalian antigen-presenting associated cells;
   b. culturing the resulting cells in a culture vessel coated with a sugar chain-containing polymer; and
   c. detaching the cells by shaking the culture vessel without treating the cells with enzyme and without using a cell detaching tool.

2. The preparation method according to 1 above, wherein a culture liquid used in the step b contains a physiologically active substance and an antigen.

3. The preparation method according to 1 or 2 above, which further comprises the following step:
   d. culturing the detached cells in a culture liquid containing a physiologically active substance and an antigen.

4. The preparation method according to 2 or 3 above, wherein the physiologically active substance is selected from the group consisting of PMA, PHA, Hasumi vaccine M, GM-CSF, IFN-α, TNF-α, IL-3, IL-4, SCF, TGF-α, TGF-β1, Mycobacterium tuberculosis cell component, LPS, Picibanil, poly I: C and hyaluronic acid complex fragment.

5. The preparation method according to 2 or 3 above, wherein the antigen is selected from the group consisting of cancer cell lysate, cancer cell acid-extracted peptide, cancer cell-associated synthetic peptide, IgM idiotype, MUT1 peptide, HPV16-E7 peptide, p53 mutant peptide, MART1, gp100, chitosinase peptide, TRP1, TRP2, tyrosinase, PSA, proteinase 3, MAGE-1, MAGE-3, BAGE, GAGE-1, GAGE-2, NY-ESO-1, β-catenin, MUM-1, TPI, CASP-8, KIAA0205, bcr-abl (0210), TEL-AML1, Her2/new, ras, WT1, CEA, SART-1, KIAAO156, cyclophilin B, Lck, MUC-1, mutant HLA-A2, HA1, HA2, H-Y and LacZ.

6. The preparation method according to any one of 1 to 5 above, wherein the antigen-presenting associated cells include dendritic cells or Langerhans cells.

7. The preparation method according to any one of 1 to 6 above, wherein the mammal is a human.

8. The preparation method according to any one of 1 to 7 above, wherein the sugar chain-containing polymer is PVLA, P(VLA-co-SU), PVGlcNAc, PVMA, PVCA, PVMea, PVLam or PVMan.

9. The preparation method according to any one of 1 to 8 above, wherein the step c comprises the following steps:
    c1. removing the culture liquid and adding PBS containing EDTA;
    c2. allowing the vessel to stand undisturbed for 10 minutes at 4 to 10° C.; and
    c3. detaching the cells by shaking the vessel.

10. The preparation method according to 9 above, wherein a concentration of the EDTA is 0.02 mM to 20 mM.

11. The preparation method according to 9 or 10 above, wherein the liquid depth of the PBS containing EDTA is 2 to 5 mm.

12. Adoptive immune cells obtained by the preparation method according to any one of 1 to 11 above.

13. A culture vessel coated with a sugar chain-containing polymer for use in the preparation-method according to any one of 1 to 11 above.

14. The culture vessel according to 13 above, wherein the sugar chain-containing polymer is PVLA, P(VLA-co-SU), PVGlcNAc, PVMA, PVCA, PVMea, PVLam or PVMan.

15. A kit for preparing an adoptive immune cell vaccine comprising the culture vessel according to 13 or 14 above.

16. The kit according to 15 above, which further comprises a cell separation tube, an antigen and/or a culture liquid.

17. A method for treating a malignant tumor, type I diabetes, atopic allergic diseases or infections using the adoptive immune cells according to 12 above.

18. A medicine for treating a malignant tumor, type I diabetes, atopic allergic diseases or infections comprising the adoptive immune cells according to 12 above.

Figure 1:
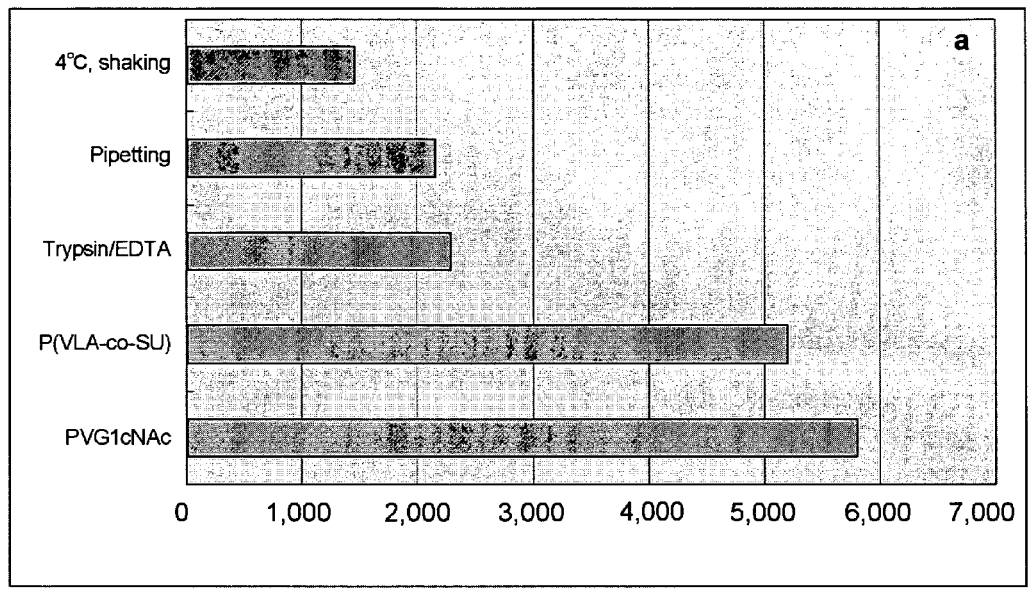
FIG. 1 shows a comparison of CD80/86, CD11c and I-$A^d$ positive cells detached and recovered from a 1° MLR culture. The x axis of a represents the numbers of CD80/86, CD11c and I-$A^d$ positive cells which were detached and recovered, while the x axis of b represents the percentages of CD80/86, CD11c and I-$A^d$ positive cells which were detached and recovered.
Figure 1:
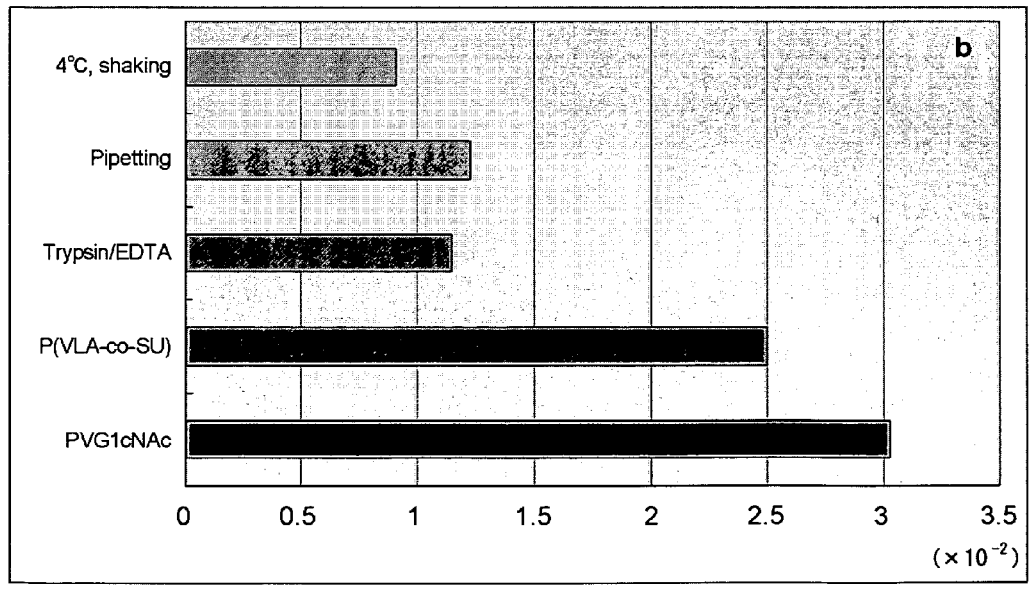

Experiment group A comprises detaching and recovering cells from the culturing surface of a culture flask coated with PVGlcNAc by shaking it in EDTA/PBS(−), followed by staining the cells remaining on the culturing surface with Giemsa stain and photographing with a microscope.

A-1: Magnification: 40×. Within the frame, it is shown differences in residual cell densities following detachment at the boundary between a polymer uncoated surface (circular) and a coated surface.

A-2: Magnification: 100×. Arrows indicate differences in residual cell densities following detachment at the boundary between a polymer uncoated surface (circular) and a coated surface.

A-3: Magnification: 200×. Arrows indicate differences in residual cell densities following detachment at the boundary between a polymer uncoated surface (circular) and a coated surface.

Experiment group B comprises detaching and recovering cells from the culturing surface of a culture flask coated with P(VLA-co-SU) by shaking it in EDTA/PBS(−), followed by staining the cells remaining on the culturing surface with Giemsa stain and photographing with a microscope.

B-1: Magnification: 40×
B-2: Magnification: 100×
B-3: Magnification: 200×

Experiment group C comprises detaching and recovering cells from the culturing surface of a commercially available culture flask with a protease (trypsin), followed by staining the cells remaining on the culturing surface with Giemsa stain and photographing with a microscope.

C-1: Magnification: 40×
C-2: Magnification: 100×
C-3: Magnification: 200×

Experiment group D comprises detaching and recovering cells from the culturing surface of a commercially available culture flask by shaking it in EDTA/PBS(−), followed by staining the cells remaining on the culturing surface with Giemsa stain and photographing with a microscope.

D-1: Magnification: 40×
D-2: Magnification: 100×
D-3: Magnification: 200×

Experiment group E comprises detaching and recovering cells from the culturing surface of a commercially available culture flask by strongly blowing EDTA/PBS(−) with a pipette, followed by staining the cells remaining on the culturing surface with Giemsa stain and photographing with a microscope.

E-1: Magnification: 40×. Arrow indicates the portion where the cells were detached along the direction in which EDTA/PBS(−) was blown with the pipette.

E-2: Magnification: 100×.

E-3: Magnification: 200×. Arrows indicate the ruffled edges of the adhered cells being curled up along the direction in which EDTA/PBS(−) was blown with the pipette.

BEST MODE FOR CARRYING OUT THE INVENTION

The following provides a detailed explanation of the present invention.

The present invention relates to a method for preparing adoptive immune cells comprising the following steps:
a. obtaining mammalian antigen-presenting associated cells;
b. culturing the resulting cells in a culture vessel coated with a sugar chain-containing polymer; and
c. detaching the cells by shaking the culture vessel without treating the cells with enzyme and without using a cell detaching tool.

The term "antigen-presenting" in the present invention refers to decomposing an antigen incorporated from outside cells, expressing complex molecules of the resulting fragments and MHC molecules on a cell membrane, and then presenting them to naive immune cells for expressing antigen-specific immunity.

The term "antigen-presenting associated cells" in the present invention refers to cells having the ability to present antigen or cells capable of differentiating into cells having the ability to present antigen.

Cells having the ability to present antigen refer to all cells which have the ability to present antigen, examples of which include, but are not limited to, thymic epithelial cells, monocytes, monocyte-derived cells, macrophages, dendritic cells and Langerhans cells.

Cells capable of differentiating into cells having the ability to present antigen refer to all cells capable of acquiring the ability to present antigen, examples of which include, but are not limited to, thymic epithelial cells, stem cells, hematopoietic stem cells, ES cells, ES cultured cells, bone marrow progenitor cells, myeloblasts and myeloid progenitor cells.

Antigen-presenting associated cells of the present invention are able to be acquired from tissue or body fluid in which they are contained. Specific examples include all biological resources obtainable the antigen-presenting associated cells, but are not limited to, tissue and body fluid containing stem cells or hematopoietic stem cells, early fetal yolk sac, fetal liver from age 2 months to birth, fetal spleen from age 2 months to birth, bone marrow including that starting at fetal age 2 months and after birth, cord blood, peripheral blood, peripheral blood during recovery from a serious infection, and peripheral blood following administration of a hematinic such as GM-CSF.

Any conventionally known method for acquiring cells can be used to acquire the aforementioned cells, examples of which include collection of whole blood or bone marrow fluid, collection of monocytes from the peripheral blood by apheresis, and proliferation of monocyte-derived primary-cultured cells or cell lines.

The culture liquid used in the preparation method of the present invention can contain a physiologically active substance and antigen.

In the present invention, a "physiologically active substance" refers to a substance capable of regulating the physiological activity of cells, tissue or organs, examples of which include proteins in the manner of enzymes, toxins, cytotoxic proteins, cytokines, chemokines, growth factors and interferon; polypeptides; oligopeptides; sugars; nucleotides in the manner of human genes, animal genes, microbe genes, virus genes, antisense DNA and antisense RNA; amino acids; and, fatty acids.

More specifically, physiologically active substances maybe PMA (phorbol 12-myristate 13-acetate), LPS, Picibanil, Hasumi vaccine M, PHA, poly I:C, TSST-1 (toxic shock syndrome toxin-1), cholera toxin B subunit, GM-CSF, M-CSF, IFN-α, IFN-β, IFN-γ, TNF-α, IL-1β, IL-3, IL-4, IL-6, IL-7, IL-12, SCF, TGF-α, TGF-β1, *Mycobacterium tuberculosis* cell component, lymphocytic choriomeningitis virus, influenza virus, *Staphylococcus bacteria*, pertussis bacteria, *toxoplasma gondii*, cell and bacteria products (such as lipopolysaccharides, lipoteichoic acid, bacterial heat shock protein, CpG motif, mycobacteria trehalose, mycolic acid, *toxoplasma gondii*-derived soluble antigen, *Leishmania* liposome protein, double-strand DNA), hyaluronic acid binding fragments, eotaxin-1α, MIP-1α, MIP-1β, MIP-3α, MCP-1, MCP-2, ELC, RANTES, SLC, BACA-1, IL-8, MIP-2α, MIP-2β, MIG, SDF-1α and SDF-1β.

In the present invention, an "antigen" refers to a substance which induces the formation of a specific antibody in a vertebrate host, or a substance which induces the generation of a specific lymphocyte population which reacts with that substance, and includes organic and inorganic compounds provided they are able to function as antigens. Examples of antigens include proteins, nucleic acids, carbohydrates, lipids or fragments or derivatives thereof.

More specifically, examples of antigens include cancer cell lysate, cancer cell acid-extracted peptide, IgM idiotype, β-Gal protein, MUT1 peptide, HPV16-E7 peptide, OVA peptide, p53 mutant peptide, MART1, gp100, chitosinase peptide, TRP1, TRP2, tyrosinase, PSA, proteinase 3, MAGE-1, MAGE-3, BAGE, GAGE-1, GAGE-2, NY-ESO-1, β-catenin, MUM-1, CDK4, TPI, CDC27, LDLR-FUT, CASP-8, KIAA0205, EF2, bcr-abl (0210), TEL-AML1, Her2/new, ras, WT1, CEA, SART-1, KIAA0156, cyclophilin B, Lck, F4.2, MUC-1 mucin, RAGE, HPV16-E7, EBV-EBNA-2,3,4,6, EBV-LMP2, HTLV-1tax, mutant HLA-A2, HA1, HA2, H-Y, HB1, PRAME, GnT-V, p15, LacZ, MART-1, AFP, TRP-2 and Net.

The step of culturing detached cells in culture liquid containing a physiologically active substance and antigen can also be carried out following the aforementioned cell detaching step.

A preferable mammal of the present invention is a human.

The sugar chain-containing polymer used in the present invention is exemplified by PVLA. PVLA (poly(p-N-vinyl-benzyl-D-1-actonamide)) is a polystyrene derivative having lactose in a side chain thereof, the β-galactose in the lactose side chain is specifically recognized by an asialoglycoprotein receptor (ASGPR) present on the membrane surface of liver parenchymal cells, and is known to be extremely important and useful for demonstration of function and organization of hepatocytes.

PVLA is represented by the structural formula shown below.

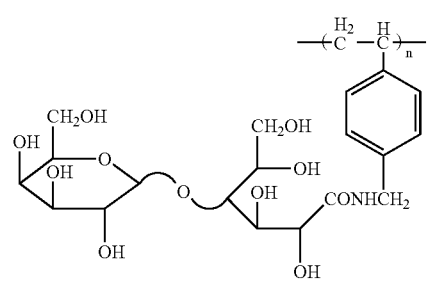

Polymer synthesis is carried out by dissolving a monomer in a solvent such as DMSO, toluene or cyclohexane, and after removing the oxygen by deaeration treatment, adding an initiator such as AIBN or BPO. Subsequently, the polymer can be easily synthesized by reacting for a suitable amount of time of 2 hours or more by heating at a temperature equal to or higher than the cleavage temperature of the initiator in a sealed vessel. In the case of a sugar chain monomer such as VLA (N-p-vinylbenzyl-O-β-D-galactopyranosyl-(1-4)-D-gluconamide), although a comparatively highly polar solvent such as DMSO or DMF is used preferably, the solvent is not limited to such solvents.

In the case of using a solvent in which VLA dissolves but the monomer to be copolymerized does not dissolve, the polymer is synthesized either by selecting a solvent in which both dissolve, or mixing solutions in which each one is dissolved.

In another aspect of the present invention, VGlcNAc (N-p-vinylbenzyl-O-β-2-acetoamido-2-deoxy-D-glucopyranosyl-(1-4)-2-acetoamido-2-deoxy-D-gluconamide), VMA (N-p-vinylbenzyl-O-α-D-glucopyranosyl-(1-4)-D-gluconamide), VCA (N-p-vinylbenzyl-O-β-D-glucopyranosyl-(1-4)-D-gluconamide), VMan (N-p-vinylbenzyl-O-β-D-mannopyranosyl-(1-4)-D-mannoamide), VMea (N-p-vinylbenzyl-O-α-D-galactopyranosyl-(1-6)-D-gluconamide), VLAm (N-p-vinylbenzyl-O-α-D-glucopyranosyl-(1-3)-D-gluconamide) or a commercially available monomer can be used alone or in the form of a copolymer instead of VLA.

Structural formula of PVGlcNAc:

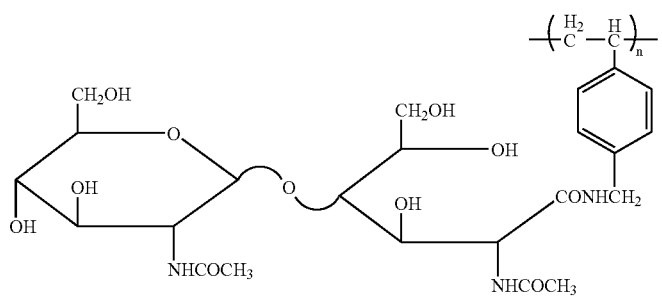

Structural formula of P (VLA-co-SU):

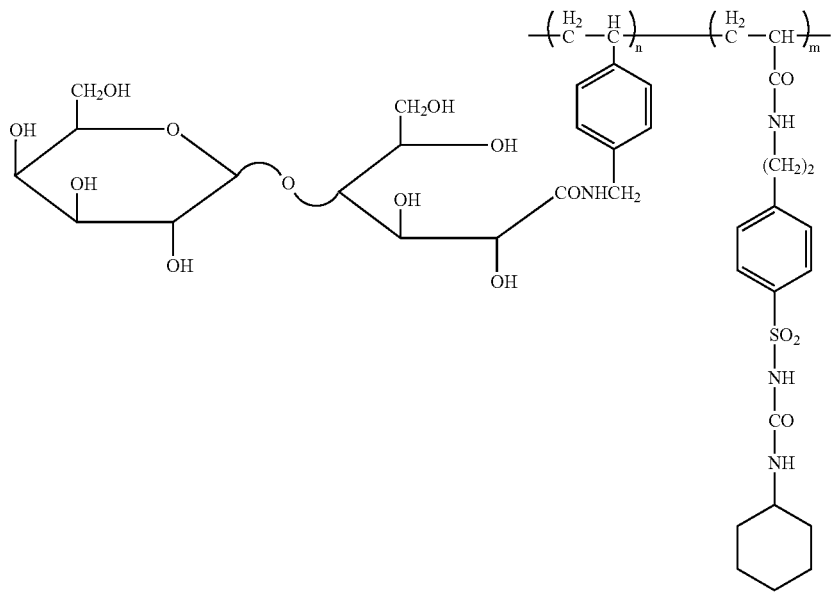

A preferable example of a sugar chain-containing polymer of the present invention is P(VLA-co-SU) or PVGlcNAc.

The cell detaching step of the present invention can contain the following steps:

c1. removing the culture liquid and adding PBS containing EDTA;
c2. allowing the vessel to stand undisturbed for 10 minutes at 4 to 10° C.; and
c3. detaching the cells by shaking the vessel.

The concentration of EDTA is preferably 0.02 to 20 mM.
The liquid depth of PBS containing EDTA is preferably 2 to 5 mm.

In addition, the present invention relates to adoptive immune cells obtained by the preparation method of the present invention.

In addition, the present invention relates to a culture vessel coated with PVLA, and preferably P(VLA-co-SU) or PVGlcNAc, for use in the preparation method of the present invention.

The sugar chain-containing polymer can be coated onto a Petri dish in the form of a suitable aqueous solution. Although preferably used in the form of a 0.01% by weight solution of pure water or PBS, the aqueous solution is not limited thereto. Coating can be carried out by adding a suitable amount of sugar chain-containing polymer solution corresponding to the size of the Petri dish. At this time, preferably a liquid depth should be maintained so that the Petri dish is covered with liquid, and although a liquid depth of 1 to 5 mm is used preferably, the liquid depth is not limited thereto. Coating can be carried out by treating it for 1 to 24 hours, preferably coating is carried out by treating it for 2 hours, but not limited thereto.

In addition, the present invention relates to a kit which comprises the aforementioned culture vessel for preparing an adoptive immune cell vaccine. The kit of the present invention can also contain a centrifuge tube for cell separation, antigen and/or culture liquid.

In addition, the present invention relates to a method for treating malignant tumors, type I diabetes, atopic allergic diseases or infections using the adoptive immune cells of the present invention.

Specific examples of the treatment method of the present invention include, but are not limited to, those indicated below.

1. A cell fraction containing mainly of a peripheral blood mononuclear cell component is collected by apheresis after waiting for recovery of hematopoiesis of a patient from which a tumor was excised following tumor excision. Recovery of hematopoiesis is confirmed by a supervising physician according to the number of each component cell in the peripheral blood.

2. The peripheral blood mononuclear cell component, which is free of erythrocytes, platelets and so forth, is obtained by fractionating the blood cell fraction obtained by apheresis using density gradient centrifugation (separation liquid: Lymphosepar I, centrifugation conditions: 400×g, 30 minutes). The cells of this component are referred to as PBMNL (peripheral blood mononuclear leukocytes), and will be described later.

3. After washing the resulting PBMNL, culturing is started in a culture liquid to which has been added a physiologically active substance (such as PMA, PHA, Hasumi vaccine M, GM-CSF, IFN-α, TNF-α, IL-3, IL-4, SCF, TGF-α, TGF-β1, *Mycobacterium tuberculosis* cell component, LPS, Picibanil, poly I:C or hyaluronic acid complex fragment) (induction of differentiation and maturation of dendritic cells). A plastic culture vessel coated with a sugar chain-containing polymer (such as P(VLA-co-SU) or PVGlcNAc) is used as the culture vessel. Fresh culture liquid is added to all cultured cells every 3 days throughout the culturing period.

On day 7 of culturing, in addition to the fresh culture liquid, a cancer-associated antigen solution (such as cancer cell lysate, cancer cell acid-extracted peptide, cancer cell-associated synthetic peptide, IgM idiotype, MUT1 peptide, HPV16-E7- peptide, p53 mutant peptide, MART1, gp100, chitosinase peptide, TRP1, TRP2, tyrosinase, PSA, proteinase 3, MAGE-1, MAGE-3, BAGE, GAGE-1, GAGE-2, NY-ESO-1, β-catenin, MUM-1, TPI, CASP-8, KIAA0205, bcr-abl (0210), TEL-AML1, Her2/new, ras, WT1, CEA, SART-1, KIAA0156, cyclophilin B, Lck, MUC-1, mutant HLA-A2, HA1, HA2, H-Y or LacZ) is added followed culturing for an additional 7 days (induction of cancer-specific antigen-presenting cells).

On the final day of culturing, the cells are detached and recovered from the culture vessel. Detachment and recovery of adhered cells are carried out by shaking. Detachment and recovery by shaking can be carried out according to the method described below. Suspended cells are recovered into a centrifuge tube, and the bottom of the flask is rinsed once with EDTA/PBS(−). Next, EDTA/PBS(−) is added so that the depth from the bottom of the flask is 2 to 5 mm, followed by allowing to stand undisturbed for 10 minutes at 4° C. Subsequently, the flask is shaken for 10 minutes with a shaker under conditions of an amplitude of 2.0 to 4.0 cm and speed of 130 to 160 times/minute. Following shaking, the detached cells are recovered. The flask is then washed twice with EDTA/PBS(−), and the detached cells are collected in the aforementioned centrifuge tube. The resulting cells are referred to as cancer antigen-specific antigen-presenting cells.

4. Induction and culturing of activated T cells are carried out simultaneous to and in parallel with the induction and culturing step of the cancer antigen-specific antigen-presenting cells. The procedure is described below.

The PBMNL obtained in the previous two steps is cultured for 3 days in the culture liquid in which PHA is added (final concentration: 10 μg/ml) to fresh culture liquid. A plastic culture vessel coated with a sugar chain-containing polymer (e.g., P(VLA-co-SU) or PVGlcNAc) is used as the culture vessel. Fresh culture liquid is added to all of the cultured cells every 2 days throughout the culturing period. After 3 days, inomycin was added to each culture (final concentration: 1 μg/ml) followed by additionally culturing for 3 days.

The cells in the culture vessel are collected at completion of culturing. Detachment and recovery of adhered cells are carried out by shaking. Detachment and recovering the adhered cells by shaking can be carried out in the manner described below.

Suspended cells are recovered in a centrifuge tube, and the bottom of the flask is rinsed once with EDTA/PBS(−). Next, EDTA/PBS(−) is added so that the depth from the bottom of the flask is 2 to 5 mm, followed by allowing to stand undisturbed for 10 minutes at 4° C. Subsequently, the flask is shaken for 10 minutes with a shaker under conditions of an amplitude of 2.0 to 4.0 cm and speed of 130 to 160 times/minute. Following shaking, the detached cells are recovered. The flask is then washed twice with EDTA/PBS(−), and the detached cells are collected in the aforementioned centrifuge tube. The resulting cells are referred to as AT cells.

5. The cancer antigen-specific antigen-presenting cells and the AT cells are washed with fresh culture liquid.

After confirming the presence or absence of pyrogen and bacterial contamination, both cells are administered to the same person from which the PBMNL were obtained. The present invention relates also to a medicine for treating a malignant tumor, type I diabetes, atopic allergic diseases or infections using the adoptive immune cells.

The aforementioned medicine can be prepared using the adoptive immune cells of the present invention as it is, or in the form of a pharmaceutical composition by mixing the adoptive immune cells of the present invention with known pharmaceutically acceptable carriers (including a vehicle, extender, binder or lubricant) or commonly used additives. The pharmaceutical composition can be administered orally or parenterally corresponding to the prepared drug form (examples of oral preparations: tablets, pills, capsules, powders, granules and syrups; examples of parenteral preparations: injections, intravenous drips, topical preparations, nose drops, eye drops, inhalants and suppositories). In addition, the dosage varies according to the type of active ingredient, administration route, and age, body weight and symptoms of administered subject or patient.

EXAMPLES

The following provides a detailed explanation of the present invention through examples thereof.
<Materials and Methods>
Animals
1) Mice:
Male, four-week-old C57B1/6 and BALB/c mice were purchased from Oriental Yeast Co., Ltd.
Cells
1) Preparation of Mouse Mononuclear Leukocytes
BALB/c mice were sacrificed by severing a cervical vertebrae followed by aseptic removal of the spleen, thymus and celiac lymph nodes. Suspended cells were obtained from the resulting tissues by gently breaking up the tissue in culture liquid with two slide glasses. After removing tissue fragments from the cell suspension by filtering through cotton, the cell suspension was centrifuged for 7 minutes at 300×g and 4° C. Following centrifugation, the supernatant was removed and the cells were re-suspended in culture liquid. This series of operations was repeated three times to remove all tissue and cell fragments except for the cells. After washing, the spleen cells, thymus cells and lymph node cells were pooled. In this experiment, these pooled cells are referred to as mononuclear leukocytes (MNL).
2) Preparation of Concanavalin A Blast (ConA Blast) Cells
ConA (Sigma Chemical Co., Cat. No. C-0412) was added to the $1-5 \times 10^6$ cells/ml of the suspended cells to a final concentration of 2 μg/ml, and cultured in an incubator under conditions of 37° C. and 5% $CO_2$. The suspended cells were recovered from the culture vessel into a 50 ml centrifuge tube 48 hours later and washed 5 times with culture liquid.
3) Preparation of Mitomycin C (MMC) Treated Cells
MMC (Sigma Chemical Co., Cat No. M-0503) was added to $1-5 \times 10^6$ cells/ml of the suspended cells to a final concentration of 50 μg/ml and allowed to stand undisturbed at 37° C. The cells were washed with culture liquid 60 minutes later and then re-suspended in culture liquid.
4) Immunofluorescent Staining
The suspension of immunostained cells was centrifuged in a 15 ml centrifuge tube (300×g, 4° C., 7 minutes). The supernatant was discarded to obtain a pellet. The pellet was then broken up gently followed by the addition of Fc Block™ (Nippon Becton Dickinson Company, Ltd., Cat. No. 01241D) at 2 μl per $1 \times 10^6$ cells. Next, 2 μl of PE-anti-mouse I-Ad (Nippon Becton Dickinson Company, Ltd., Cat. No. 06035A), 2 μl of FITC-anti-mouse CD11c (Nippon Becton Dickinson Company, Ltd., Cat No. 557400), 2 μl of biotin-anti-mouse CD80 (Nippon Becton Dickinson Company, Ltd., Cat. No. 553867) and 2 μl of biotin-anti-mouse CD86 (Nippon Becton Dickinson Company, Ltd., Cat. No. 553690) were added per $1 \times 10^6$ cells. This mixture was then allowed to stand undisturbed for 30 minutes on ice. Following the reaction, 10 ml of washing buffer was added, the mixture was centrifuged at 300×g and 4° C. for 7 minutes and the supernatant was discarded. This procedure was repeated three times. 2 μl of streptoavidin-Cy-Chrome (Nippon Becton Dickinson Company, Ltd., Cat. No. 554062) was added to the resulting cell pellet followed by allowing to stand undisturbed for 30 minutes on ice. Following the reaction, 10 ml of washing buffer was added to the cells, the mixture was centrifuged at 300×g and 4° C. for 7 minutes and the supernatant was discarded. This procedure was repeated on the cells three times after which the cells were re-suspended in 1 ml of washing buffer followed by analyzing those cells positive for fluorescent labeled antibody by flow cytometry (Nippon Becton Dickinson Company, Ltd., Model FACS Calibur™).
5) Primary Mixed Leukocyte Reaction (1° MLR)
Antigen-specific antigen-presenting cells to alloantigen were obtained by 1° MLR culturing. The procedure was carried out as described below. 12 ml of MNL derived from BALB/c mice ($H-2^d$) adjusted to $5 \times 10^6$ cells/ml, and 12 ml of MMC-treated C57B1/6 ($H-2^b$)-derived MNL adjusted to $5 \times 10^6$ cells/ml were added to a 75 $cm^2$ culturing flask followed by the addition of interleukin 2 (Sigma Chemical Co., Cat. No. I-0523) to a final concentration of 20 ng/ml and culturing at 37° C. in 5% $CO_2$.

Flasks manufactured by Nippon Becton Dickinson Company, Ltd., (Cat. No. 353136) were used as culturing flasks for adhered cells used in conventional detachment and recovery, while flasks manufactured by Nippon Becton Dickinson Company, Ltd., (Cat. No. 353133) coated with each test polymer were used as the flasks coated with the test polymers. Culturing was carried out for 12 days, and 2 ml each of fresh culture liquid was added every 3 days.
6) Detachment and Recovery of Cells from 1° MLR Culturing Flasks
Cells were recovered from each of the flasks in the manner described below 12 days after 1° MLR culturing.

With respect to the flasks coated with polymer, the suspended cells were recovered in a 50 ml centrifuge tube and the bottoms of the flasks were rinsed once with EDTA/PBS(−). Next, EDTA/PBS(−) was added to a depth of 2 to 5 mm from the bottom of the flasks and allowed to stand undisturbed for 10 minutes at 4° C. Subsequently, the flasks were shaken for 10 minutes under conditions of an amplitude of 3.0 cm and speed of 130 to 160 times/minute with a shaker (Nissin Scientific Corporation, Reciprocal Shaker NA-201). Following shaking, the cells that detached from the flasks were recovered. The flasks were additionally washed twice with 5 ml of EDTA/PBS(−), and the detached cells were collected in the aforementioned centrifuge tube.

The cells detached and recovered by the enzyme treatment method were prepared in the manner described below.

Suspended cells following 1° MLR culturing were recovered from flasks for cell adhesion not coated with polymer into a 50 ml centrifuge tube. 5 ml of EDTA/PBS(−) was added to the culturing surfaces of the flasks and the flasks were tilted gently back and forth gently. This procedure was repeated 4 to 5 times. The cells that were suspended by this procedure were also pooled in the same centrifuge tube. 5 ml of trypsin/EDTA was added to the flasks followed by allowing to stand undisturbed for 5 to 10 minutes at room temperature. When the time came, the flasks were gently tilted back and forth (rinsed), and this procedure was repeated 5 to 6 times. The cells that were suspended as a result of this procedure were recovered into a 50 ml centrifuge tube to which 10 ml of culture liquid had added in advance. The flask culturing surface was further rinsed twice with 5 ml of EDTA/PBS (−). The resulting detached cell groups were pooled for each experiment group.

In the pipetting method, suspended cells following 1° MLR culturing were recovered from the flask for adhered cells into a 50 ml centrifuge tube. 5 ml of EDTA/PBS(−) was added to the flask culturing surface followed by gently tilting back and forth, and this procedure was repeated 4 to 5 times. The cells that were suspended by this procedure were also pooled in the same centrifuge tube. Next, the entire culturing surface was washed by vigorously blowing on EDTA/PBS(−) with a 10 ml plastic pipette (Nippon Becton Dickinson Company, Ltd., Cat. No. 357551). This washing was repeated three times while replacing with fresh EDTA/PBS(−) each time. The resulting cells by each washing were pooled for each experiment group.

7) Cytotoxicity Test

Measurement of the number of non-viable target cells damaged by cytotoxic T cells (CTL) was carried out using 7-amino-actinomycin D (7-AAD, Nippon Becton Dickinson Company, Ltd., Cat. No. 555816). In the procedure, a pellet of $1 \times 10^6$ cells was mixed with 20 μl of FITC-anti-mouse H-2 $D^b$ antibody, which specifically reacts with C57B1/6 target MNL, and 20 μl of Fc Block™, followed by allowing to react for 30 minutes at 4° C. Following the reaction, the cells were washed once with 10 ml of washing buffer followed by the addition of 20 μl of 7-AAD and allowing to stand undisturbed at room temperature. Ten minutes later, the ratio of H-2 $D^b$ positive cells and the number of cells were determined by flow cytometry (Nippon Becton Dickinson Company, Ltd., Model FACS Calibur™). This value indicates the target cells damaged by CTL to be determined.

Reagents

1) PVLA Synthesis

VLA Synthesis:

Reaction Scheme 1: Synthesis of Vinylbenzyl Phthalimide

One kg of chloromethyl styrene was dissolved in 3.2 L of DMF in a round-bottom recovery flask of an appropriate volume followed by the addition of 1.2 kg of potassium phthalimide. This was allowed to react for 4 hours at 50° C. After distilling off the DMF using an evaporator, 4.5 L of benzene was added to dissolve the residue. The benzene was washed several times with 0.2 N NaOH solution (total volume: 3.25 L). The benzene was further washed several times with water (total volume: 3.25 L), and after drying with $Na_2SO_4$ and forth, the solvent was distilled off using an evaporator. The residue was then recrystallized from methanol to obtain the target substance. Yield: 1.5 kg Reaction Scheme 2: Synthesis of Vinylbenzylamine One kg of vinylbenzyl phthalimide was dissolved in 2.7 L of ethanol in an separable flask of appropriate volume followed by heating and refluxing in the presence of flowing nitrogen. A solution of 0.36 kg of 80% hydrazine monohydrate in 545 ml of ethanol was dropped in using a dropping funnel (dropping time: about 40 minutes). The reaction was carried out for 90 minutes by heating and refluxing. Following completion of the reaction, the resulting solid was filtered out, and after dissolving by the addition of KOH solution (1 kg in 6.5 L $H_2O$), the solution was extracted with ether (total volume: 3.6 L×3). The ether layer was further washed with 2% $K_2CO_3$ solution, and additionally washed several times with water. After drying the ether layer over $Na_2SO_4$, the ether was distilled off, and the residue was distilled under reduced pressure.

Boiling point: 72-73° C./3 mmHg

Yield: 0.45 kg

Reaction Scheme 3: Synthesis of Lactose Lactone 12 kg of lactose was dispersed in 300 ml of methanol and heated to 40° C. A methanol solution containing 18 g of iodine was dropped therein and allowed to react for 40 minutes. A 4 N KOH methanol solution was added thereto until the iodine was no longer colored. After filtering off the precipitate and washing several times with cold methanol, it was washed with ether and weighed.

Subsequently, the resulting crystals were dissolved in a very small amount of water, and applied to an Amberlite 120B proton ion exchange resin to isolate the acidic fraction. Methanol and ethanol were added to the resulting aqueous solution and then evaporated. After allowing to dry completely, methanol and ethanol were again added to dissolve the solid and again evaporated. This procedure was repeated several times to produce lactose lactone.

Reaction Scheme 4: Synthesis of VLA

After dissolving 1 kg of lactose lactone in 5.4 L of methanol in a round-bottom recovery flask of appropriate volume at 70° C., 0.4 kg of vinylbenzylamine was added and allowed to react for 120 minutes at 70° C. Following completion of the reaction, 21.7 L of acetone was added to precipitate the target substance. After allowing this to stand undisturbed for several hours at 4° C., the precipitate was filtered out and recrystallized from methanol. Yield: 1.1 kg Polymer Synthesis The VLA was dispensed into a vacuum reaction tube. After completely dissolved by adding DMSO or a mixed solvent of DMSO and toluene, freezing, degassing and thawing were repeated to remove the oxygen from the solution. 1/100 mole of AIBN was added thereto to dissolve followed by sealing under reduced pressure. This was then allowed to react for 5 hours at 60° C. to synthesize the polymer.

The resulting solution was dropped into highly excess amount of methanol to precipitate the polymer. A procedure comprising dissolving it in a suitable solvent, dropping into methanol and precipitating the polymer was repeated three times.

The finally obtained polymer was dissolved in distilled water and dialyzed against highly excess amount of water. Subsequently, the target polymer was obtained by freeze-drying.

Synthesis of Cyclohexyl-4-[(2')-actylamide-ethyl]benzene sulfonyl urea (SU)

p-aminoethylbenzene sulfonamide (8 g, 30 mmol, reagent manufactured by Tokyo Chemical Industry Co. Ltd.) and acryloyl chloride (2.7 g, 30 mmol, reagent manufactured by Wako Pure Chemical Industries, Ltd.) were mixed in 15 ml of acetone followed by the addition of 15 ml of 1 N aqueous NaOH solution and allowing to, react while stirring for 2 hours at room temperature. Subsequently, the precipitate was recovered and recrystallized in methanol to obtain 4-[(2')-actylamide-ethyl]benzene sulfonamide.

The resulting 4-[(2')-actylamide-ethyl]benzene sulfonamide (3 g, 12 mmol) was dissolved in 6 ml of acetone followed by the addition of 6 ml of 1 N aqueous NaOH solution. A solution consisting of cyclohexyl isocyanate (0.9 ml, 7 mmol) dissolved in 6 ml of acetone was then added thereto and allowed to react for 16 hours at room temperature. After neutralizing with hydrochloric acid, the resulting crystals were recovered and recrystallized from methanol to obtain the target substance.

Copolymer

Monomer to be copolymerized with VLA was weighed at a molar ratio of 9:1, 8:2, 7:3 and so forth, and dispensed into a vacuum reaction tube. After completely dissolving by adding DMSO or a mixed solvent of DMSO and toluene, freezing, degassing and thawing were repeated to remove oxygen from the solution. 10 mmol of AIBN was then added thereto to dissolve followed by sealing under reduced pressure. This was then allowed to react for 5 hours at 60° C. to synthesize the polymer.

The resulting solution was dropped into highly excess amount of methanol to precipitate the polymer. A procedure consisting of dissolving it in a suitable solvent, dropping into methanol again and precipitating the polymer was repeated three times.

The finally obtained polymer was dissolved in distilled water and dialyzed against highly excess amount of water. Subsequently, the target polymer was obtained by freeze-drying.

In addition to the aforementioned SU, the previously described sugar chain-bound monomers and commercially available monomers can be used preferably for the comonomer.

2) Polymer Coating Method of Culturing Flask:

PVLA, P(VLA-co-SU) and PVGlcNAc were respectively prepared in the form of 0.01% by weight aqueous solutions. 5 ml aliquots of these solutions were dispensed into a flask (Nippon Becton Dickinson Company, Ltd., Cat. No. 353133). Coating treatment was then carried out for 2 hours at room temperature under protection from light. Subsequently, the polymer solution was recovered and each flask was washed three times with 10 ml of pure water prior to use in each test.

3) Culture Liquid:

0.6 g of L-glutamine (Sigma Chemical Co., Cat. No. G-5889), 1 g of HEPES (Sigma Chemical Co., Cat. No. H-4034) and 2 g of NaHCO$_3$ (Sigma Chemical Co., Cat. No. S-5761) were dissolved in 1 L of RPMI 1640 (Gibco, Cat. No. 31800-014), followed by the addition of 2-mercaptoethanol (Sigma Chemical Co., Cat. No. M-3148) to a final concentration of $5 \times 10^{-5}$ M and fetal calf serum (JRH BioSciences, Cat. No. 12103-789) to a final concentration of 10%. After mixing the aforementioned components, the mixture was sterilized by filtering with a 0.22 µm sterilization filter (Nippon Millipore Company, Sterivex-GS, Cat. No. SVGSB1010). This is referred to as the culture liquid.

4) Ca$^{++}$, Mg$^{++}$-Free PBS 10 tablets of PBS available from Oxoid Ltd. (phosphate-buffered physiological saline, Cat. No. BR0014G) were dissolved in 1 L of pure water (Nippon Millipore Company, Milli-Q Gradient Milli-Q Ultra-Pure Water System Elix 5 Kit) followed by sterilizing at high temperature and high pressure for 20 minutes at 121° C. in an autoclave. This is referred to as PBS(−).

5) 0.2% EDTA/PBS(−)

2 g of EDTA (EDTA-4Na, Wako Pure Chemical Industries, Ltd., Cat. No. 343-01883) was added to 1 L of PBS(−) followed by sterilizing at high temperature and high pressure for 20 minutes at 121° C. in an autoclave. This is referred to as EDTA/PBS(−).

6) PBS(−) Containing 0.05% Trypsin and 0.024% EDTA 0.05 g of trypsin (Sigma Chemical Co., Cat. No. T-7409) and 0.024 g of EDTA (EDTA-4Na, Wako Pure Chemical Industries Ltd., Cat. No. 343-01883) were added to and dissolved in 100 ml of PBS(−) followed by sterilizing by filtering with a 0.22 µm sterilization filter (Nippon Millipore Company, Sterivex-GS, Cat. No. SVGSB1010). This is referred to as trypsin/EDTA.

7) Washing Buffer

The washing buffer used for immunofluorescent staining was prepared in the following manner. Bovine serum albumin (Sigma Chemical Co., Cat. No. A-3059) to a final concentration of 0.1% and NaN$_3$ (Wako Pure Chemical Industries, Ltd., Cat. No. 195-11092) to a final concentration of 0.001% were added to PBS(−), and used after chilling it to 4° C.

8) Sterilization Test of Sterile Solution 1 ml of the prepared solutions was dispensed into a 15 ml sterile centrifuge tube and cultured for 8 hours at 37° C. to confirm the presence or absence of mold or bacterial growth microscopically (×100).

Equipments

1) Culturing Flasks for Suspended Cells

Untreated 75 cm$^2$ polystyrene flasks (Nippon Becton Dickinson Company, Ltd., Cat. No. 353133) were used for the flasks coated with polymer.

2) Culturing Flasks for Adhered Cells

The following flasks were used as flasks for adhered cells used as a control: Treated 75 cm$^2$ polystyrene flasks (Nippon Becton Dickinson Company, Ltd., Cat. No. 353136), treated 25 cm$^2$ polystyrene flasks (Nippon Becton Dickinson Company, Ltd., Cat. No. 353108).

3) Cell Centrifuge Tubes

The following tubes were used for the centrifuge tubes: 15 ml centrifuge tubes (Asahi Technoglass Corporation, Cat. No. 2315-015, 50 ml centrifuge tubes (Assist Co., Ltd., Cat. No. 62.548.004S).

4) Plastic Culturing Pipettes 10 ml plastic pipettes (Nippon Becton Dickinson Company, Ltd., Cat. No. 357551) were used for the plastic culturing pipettes.

<Results>

Comparison of CD80/86, CD11c and I-A$^d$-Positive Cells During 1°MLR Culturing

A comparison of CD80/86, CD11c and I-A$^d$-positive cells was carried out by three-color immunofluorescent staining. The reactive cells (H-2$^d$) and antigen cells (H-2D$^b$) were distinguished by using PE-anti-mouse I-A$^d$ antibody, which is able to identify reactive cells only. FIG. 1-$a$ shows the results of comparing the numbers of detached and recovered CD80/86, CD11c and I-A$^d$-positive cells. As shown in the Figure, the numbers of CD80/86, CD11c and I-A$^d$-positive cells detached and recovered from the flasks coated with PVGlcNAc and P(VLA-co-SU) by shaking were significantly greater than the numbers of CD80/86, CD11c and I-A$^d$-positive cells detached and recovered by enzyme treatment, pipetting or shaking using conventional commercially available flasks for adhered cells. A similar trend was also observed for the ratio (%) of the numbers of CD80/86, CD11c and I-A$^d$-positive cells recovered from 1° MLR culturing flasks to the total number of cells (FIG. 1-$b$).

Comparison of Cell Density Remaining on Culturing Surface of Flask in Each Experiment Group Following Detachment and Recovery Flasks following Detachment and recovery of cells were immediately fixed by addition of 3 ml of undiluted Giemsa stain (Mutoh Pure Chemicals Co., Ltd, Cat. No. 1500-2). After fixing for 30 to 60 minutes at room temperature (15° C.), 20 ml of tap water was added to initiate staining. Staining was carried out for 1 hour at room temperature. After staining, the culturing bottoms of the flasks were washed with tap water and allowed to air dry followed by taking photographs (Nikon Instech Co., Ltd, Coolpix Microsystem VI) with a microscope (Nikon Instech Co., Ltd, Diaphot Model), and comparing the residual cell densities.

Figure 3:
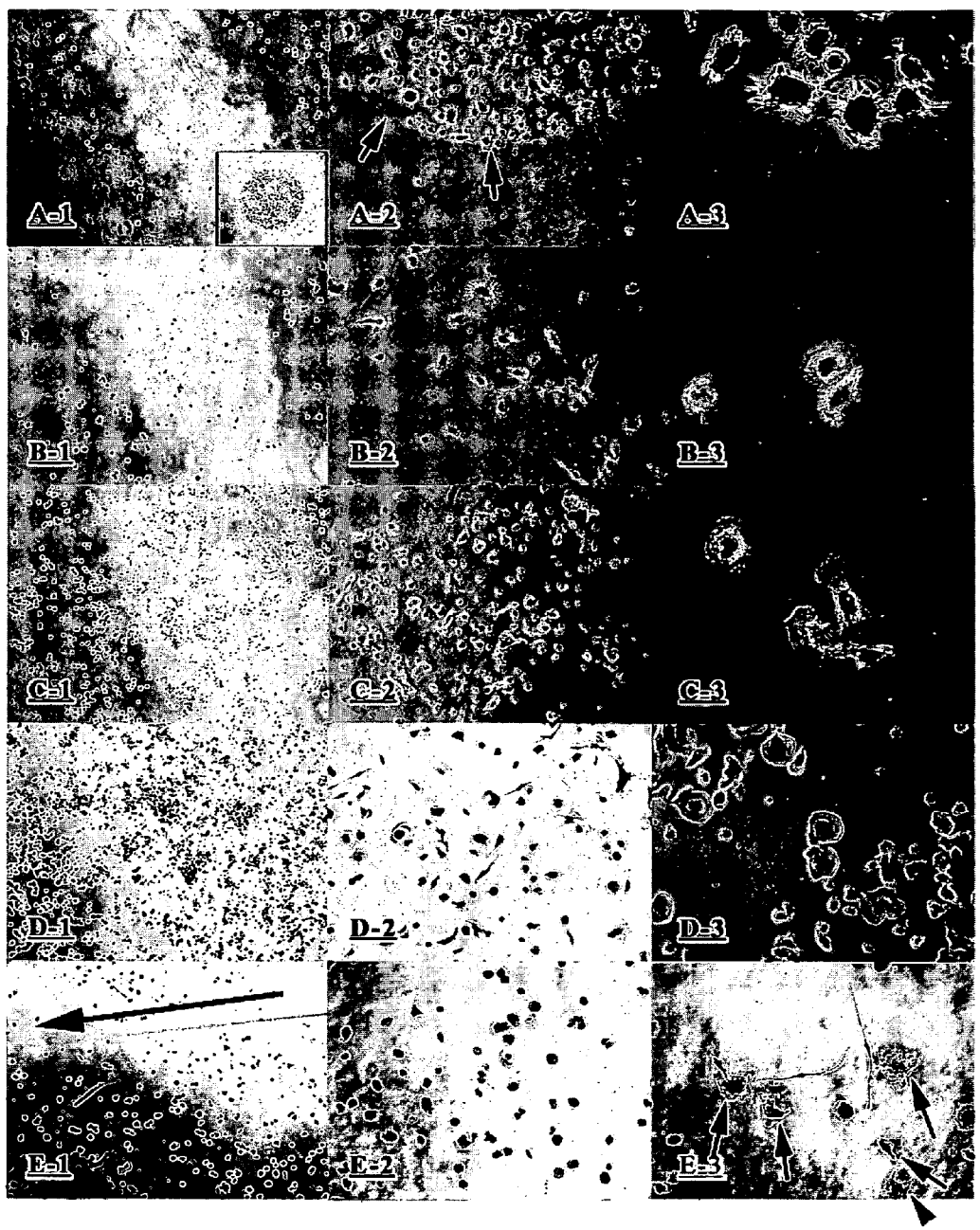
FIG. 3 shows a comparison of cell densities remaining on the flask culturing surface of each experiment group following separation and recovery of 1° MLR cultured cells.

The results are shown in FIG. 3. Colonies in which adhered cells had gathered were observed on the flask culturing surfaces following Detachment and recovery of adhered cells by enzyme treatment, pipetting and shaking from the commercially available flasks for adhered cells, and the residual densities of cells remaining on the flask surfaces were determined to be higher than those flasks from which adhered cells had been detached by shaking from the polymer-coated flasks (FIG. 3).

In the case of the pipetting method conventionally used to detach and recover cells (E-1, E-2, E-3), since cells in which the cell edges appeared to be curled up in the areas where EDTA/PBS(−) is thought to have been blown particularly strongly onto the cells were observed among the remaining cells (E-3), it is presumed that the cell membranes were damaged considerably as a result of being pulled apart.

As is observed in C-3 (×200), even in conventional detachment methods using trypsin, detachment and recovery efficiency was determined to be poor in consideration of the considerable extension of the ruffles of adhered cells and damage to cell membrane proteins (C-1, C-2).

Alloantigen-Specific Cytotoxic T Cell Test

Figure 2:
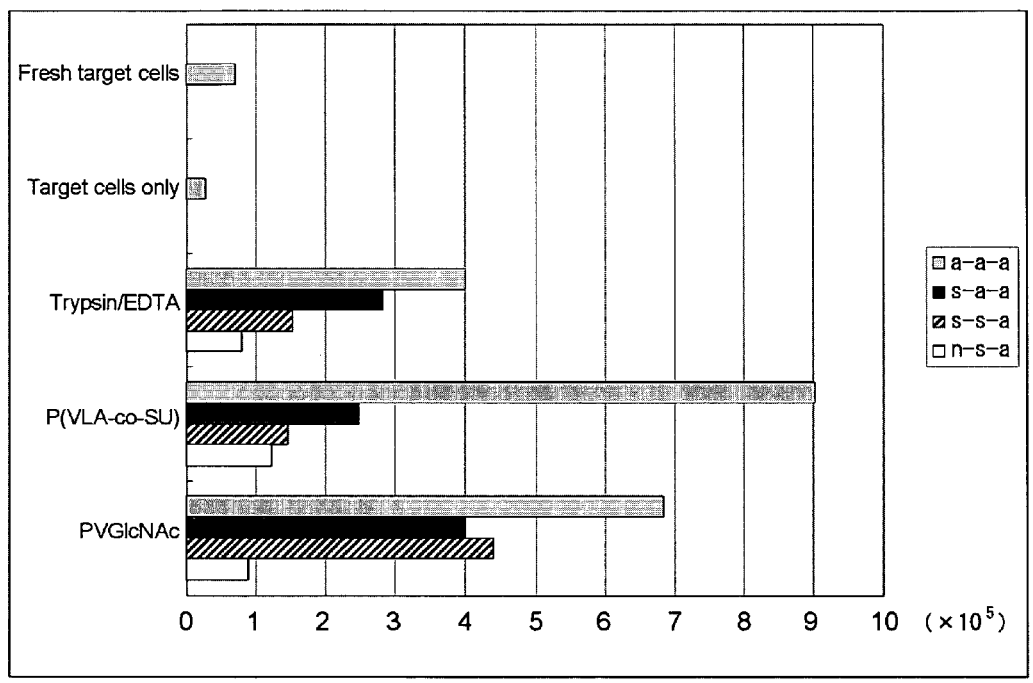
FIG. 2 shows the results of an alloantigen-specific cytotoxic T cell test. The x axis represents the number of dead target cells. The following abbreviations are used for the target cells in the graph. n: target antigen cells not added, a: alloantigen cells C56B1/6 (H-2b) MNL, s: syngeneic cells BALB/c (H-$2^d$) MNL, X-X-X: first parameter indicates 1° MLR antigen, second parameter indicates antigen used to induce CTL, and third parameter indicates target cells used in the cytotoxicity test. More specifically, a-a-a: experiment group in which alloantigen C57B1/6 MNL was used for the 1° MLR antigen, alloantigen C57B1/6 MNL was used for CTL induction, and alloantigen C57B1/6 MNL was used for the target cells of the cytotoxicity test; s-a-a: experiment group in which syngeneic BALB/c MNL was used for the 1° MLR antigen, alloantigen C57B1/6 MNL was used for CTL induction, and alloantigen C57B1/6 MNL was used for the target cells of the cytotoxicity test; s-s-a: experiment group in which syngeneic BALB/c MNL was used for the 1° MLR antigen, syngeneic BALB/c MNL was used for CTL induction, and alloantigen C57B1/6 MNL was used for the target cells of the cytotoxicity test; and, n-s-a: experiment group in which 1° MLR antigen was not added, syngeneic BALB/c MNL was used for CTL induction, and alloantigen C57B1/6 MNL was used for the target cells of the cytotoxicity test.

The antigen-presenting ability of cells obtained from 1° MLR culturing was further tested by inducing alloantigen-specific cytotoxic T cells according to the method described below. BALB/c-derived cells obtained from 1° MLR culturing were prepared to $1\times10^5$ cells/ml as antigen-presenting cells (H-$2^d$), and 1.5 ml thereof were placed in a 25 cm$^2$ flask. C57Bl/6-derived ConA blast cells were treated with MMC for use as alloantigen and added thereto. 1.5 ml of a cell suspension having a density of $1\times10^7$ cells/ml was added followed by mixing and culturing for 8 days under conditions of 37° C. and 5% $CO_2$. 2 ml of fresh culture liquid each was added on days 3 and 6 of the culturing period. On day 8 of culturing, the cell suspension was collected in a 50 ml centrifuge tube, and after washing three times with culture liquid, was re-suspended in culture liquid to $1\times10^7$ viable cells/ml. 2 ml of this suspension was then dispensed into a 15 ml centrifuge tube. 2 ml of target cells in the form of 57Bl/6-derived ConA blast cells ($1\times10^5$ cells/ml) was added to this centrifuge tube followed by culturing for 6 hours at 37° C. and 5% $CO_2$. After culturing, the suspension was centrifuged for 7 minutes at 300×g and 4° C. after which the supernatant was discarded. 20 μl of FITC-anti-mouse H-2 $D^b$ and 50 μl of Fc Block™ were added to the cell pellet followed by allowing to stand undisturbed for 30 minutes at 4° C. After allowing to react for 10 minutes, 1 ml of washing buffer was added, and the proportions of H-2 $D^b$-positive and 7AAD-positive cells were determined by flow cytometry. The results are shown in FIG. 2. Non-viable target cells (H-2 $D^b$) were confirmed by immunofluorescent staining with FITC-anti-mouse (H-2 $D^b$).

When the numbers of non-viable H-2 $D^b$-positive cells were compared for the case in which the target cells are allo cells (C57Bl/6-derived MNL) used in each of the 1° MLR and CTL induction steps (a-a-a: antigen-specific CTL induction), antigen-presenting cells prepared using a polymer-coated flask were determined to have carried out significantly higher CTL induction than conventional detachment methods using enzyme treatment. In the case of the 1° MLR cultured cells detached and recovered from flasks coated with P(VLA-co-SU), the levels of non-specific reactions (s-s-a, n-s-a) not using allo target cells in 1° MLR culturing and CTL induction were low, suggesting a high usage value for culturing, detachment and recovery of specific antigen-presenting cells. On the other hand, in the case of conventional enzyme treatment methods, the level of alloantigen-specific CTL induction was low, and the difference between antigen-specific reactions and antigen-non-specific reactions was indicated as being low in comparison with the polymer group (FIG. 2).

The invention claimed is:

1. A method for preparing adoptive immune cells comprising the following steps of:
   (a) obtaining mammalian antigen-presenting associated cells;
   (b) culturing the resulting cells from step (a) in a culture liquid contained in a culture vessel coated with a sugar chain-containing polymer; and
   (c) detaching the cells from step (b) by shaking the culture vessel without treating the cells with an enzyme and without using a cell detaching tool.

2. The method according to claim 1, wherein the culture liquid in step (b) contains a physiologically active substance and an antigen.

3. The method according to claim 2, wherein the physiologically active substance is selected from the group consisting of PMA, PHA, Hasumi vaccine M, GM-CSF, IFN-α, TNF-α, IL-3, IL-4, SCF, TGF-α, TGF-β31, Mycobacterium tuberculosis cell component, LPS, Picibanil, poly I:C and hyaluronic acid complex fragment.

4. The method according to claim 2, wherein the antigen is selected from the group consisting of cancer cell lysate, cancer cell acid-extracted peptide, cancer cell-associated synthetic peptide, IgM idiotype, MUT1 peptide, HPV16-E7 peptide, p53 mutant peptide, MART1, gp100, chitosinase peptide, TRP1, TRP2, tyrosinase, PSA, proteinase 3, MAGE-1, MAGE-3, BAGE, GAGE-1, GAGE-2, NY-ESO-1, β-catenin, MUM-1, TPI, CASP-8, KIAA0205, bcr-abl (0210), TEL-AML1, Her2/new, ras, WT1, CEA, SART-1, KTAA0156, cyclophilin B, Lck, MUC-1, mutant HLA-A2, HA1, HA2, H-Y and LacZ.

5. The method according to claim 1, wherein the mammalian antigen-presenting associated cells include dendritic cells or Langerhans cells.

6. The method according to claim 2, wherein the antigen-presenting associated cells include dendritic cells or Langerhans cells.

7. The method according to claim 3, wherein the antigen-presenting associated cells include dendritic cells or Langerhans cells.

8. The method according to claim 4, wherein the antigen-presenting associated cells include dendritic cells or Langerharis cells.

9. The method according to claim 1, wherein the mammal is a human.

10. The method according to claim 1, wherein the sugar chain-containing polymer is PVLA, P(VLA-co-SU), PVG1cNAc, PVMA, PVCA, PVMea, PVLam or PVMan.

11. The method according to claim 2, wherein the sugar chain-containing polymer is PVLA, P(VLA-co-SU), PVG1cNAc, PVMA, PVCA, PVMea, PVLam or PVMan.

12. The method according to claim 3, wherein the sugar chain-containing polymer is PVLA, P(VLA-co-SU), PVG1cNAc, PVMA, PVCA, PVMea, PVLam or PVMan.

13. The method according to claim 4, wherein the sugar chain-containing polymer is PVLA, P(VLA-co-SU), PVG1cNAc, PVMA, PVCA, PVMea, PVLam or PVMan.

14. A method for preparing adoptive immune cells comprising the following steps of:
   (a) obtaining mammalian antigen-presenting associated cells;
   (b) culturing the resulting cells from step (a) in a culture liquid contained in a culture vessel coated with a sugar chain-containing polymer; and
   (c) detaching the cells from step (b) by shaking the culture vessel without treating the cells with an enzyme and without using a cell detaching tool, wherein the step (c) comprises the following steps:
(c1) removing the culture liquid and adding PBS containing EDTA;
(c2) allowing the culture vessel to stand undisturbed for 10 minutes at 4 to 10° C.; and
(c3) detaching the cells by shaking the culture vessel.

15. The method according to claim 14, wherein the culture liquid in the step (b) contains a physiologically active substance and an antigen.

16. The method according to claim 15, wherein the physiologically active substance is selected from the group consisting of PMA, PHA, Hasumi vaccine M, GM-CSF, IFN-α, TNF-α, IL-3, TL-4, SCF, TGF-α, TGF-β1, *Mycobacterium tuberculosis* cell component, LPS, Picibanil, poly I:C and hyaluronic acid complex fragment.

17. The method according to claim 15, wherein the antigen is selected from the group consisting of cancer cell lysate, cancer cell acid-extracted peptide, cancer cell-associated synthetic peptide, IgM idiotype, MUT1 peptide, HPV16-E7 peptide, p53 mutant peptide, MART1, gp100, chitosinase peptide, TRP1, TRP2, tyrosinase, PSA, proteinase 3, MAGE-1, MAGE-3, BAGE, GAGE-1, GAGE-2, NY-ESO-1, β-catenin, MUM-1, TPI, CASP-8, KTAA0205, bcr-abl(0210), TEL-AML1, Her2/new, ras, WT1, CEA, SART-1, KIAA0156, cyclophilin B, Lck, MUC-1, mutant HLA-A2, HA1, HA2, H-Y and LacZ.

18. The method according to claim 14, wherein the EDTA has a concentration of 0.02mM to 20 mM.

19. The method according to claim 14, wherein a liquid depth of the PBS containing EDTA is 2 to 5 mm.

20. The method according to claim 1, which further comprises carrying out the following step after step (c):
(d) culturing the detached cells in a culture liquid containing a physiologically active substance and an antigen.

21. The method according to claim 20, wherein the culture liquid in step (b) contains a physiologically active substance and an antigen.

22. The method according to claim 20, wherein the physiologically active substance is selected from the group consisting of PMA, PHA, Hasumi vaccine M, GM-CSF, IFN-α, TNF-α, IL-3, IL4, SCF, TGFα, TGF-β1, *Mycobacterium tuberculosis* cell component, LPS, Picibanil, poly I:C and hyaluronic acid complex fragment.

23. The method according to claim 20, wherein the antigen is selected from the group consisting of cancer cell lysate, cancer cell acid-extracted peptide, cancer cell-associated synthetic peptide, IgM idiotype, MUT1 peptide, HPV16-E7 peptide, p53 mutant peptide, MART1, gp100, chitosinase peptide, TRP1, TRP2, tyrosinase, PSA, proteinase 3, MAGE-1, MAGE-3, BAGE, GAGE-1, GAGE-2, NY-ESO-1, β-catenin, MUM-1, TPI, CASP-8, KIAA0205, bcr-abl (0210), TEL-AML1, Her2/new, ras, WT1, CEA, SART-1, KIAA0156, cyclophilin B, Lck, MUC-1, mutant HLA-A2, HA1, HA2, H-Y and LacZ.

24. The method according to claim 20, wherein the antigen-presenting associated cells include dendritic cells or Langerhans cells.

25. The method according to claim 21, wherein the antigen-presenting associated cells include dendritic cells or Langerhans cells.

26. The method according to claim 22, wherein the antigen-presenting associated cells include dendritic cells or Langerhans cells.

27. The method according to claim 23, wherein the antigen-presenting associated cells include dendritic cells or Langerhans cells.

28. The method according to claim 20, wherein the mammal is a human.

29. The method according to claim 20, wherein the sugar chain-containing polymer is PVLA, P(VLA-co-SU), PVG1cNAc, PVMA, PVCA, PVMea, PVLam or PVMan.

30. The method according to claim 21, wherein the sugar chain-containing polymer is PVLA, P(VLA-co-SU), PVG1cNAc, PVMA, PVCA, PVMea, PVLam or PVMan.

31. The method according to claim 22, wherein the sugar chain-containing polymer is PVLA, P(VLA-co-SU), PVG1cNAc, PVMA, PVCA, PVMea, PVLam or PVMan.

32. The method according to claim 23, wherein the sugar chain-containing polymer is PVLA, P(VLA-co-SU), PVG1cNAc, PVMA, PVCA, PVMea, PVLam or PVMan.

33. A method for preparing adoptive immune cells comprising the following steps of:
(a) obtaining mammalian antigen-presenting associated cells;
(b) culturing the resulting cells from step (a) in a culture liquid contained in a culture vessel coated with a sugar chain-containing polymer;
(c) detaching the cells from step (b) by shaking the culture vessel without treating the cells with an enzyme and without using a cell detaching tool; and
(d) culturing the detached cells in a culture liquid containing a physiologically active substance and an antigen,
wherein the step (c) comprises the following steps:
(c1) removing the culture liquid and adding PBS containing EDTA;
(c2) allowing the culture vessel to stand undisturbed for 10 minutes at 4 to 10° C.; and
(c3) detaching the cells by shaking the culture vessel.

34. The method according to claim 33, wherein the culture liquid in the step (b) contains a physiologically active substance and an antigen.

35. The method according to claim 34, wherein the physiologically active substance is selected from the group consisting of PMA, PHA, Hasumi vaccine M, GM-CSF, IFN-α, TNF-α, IL-3, IL-4, SCF, TGF-α, TGF-β1, *Mycobacterium tuberculosis* cell component, LPS, Picibanil, poly I:C and hyaluronic acid complex fragment.

36. The method according to claim 34, wherein the antigen is selected from the group consisting of cancer cell lysate, cancer cell acid-extracted peptide, cancer cell-associated synthetic peptide, IgM idiotype, MUT1 peptide, HPV16-E7 peptide, p53 mutant peptide, MART1, gp100, chitosinase peptide, TRP1, TRP2, tyrosinase, PSA, proteinase 3, MAGE-1, MAGE-3, BAGE, GAGE-1, GAGE-2, NY-ESO-1, β-catenin, MUM-1, TPI, CASP-8, KIAA0205, bcr-abl (0210), TEL-AML1, Her2/new, ras, WT1, CEA, SART-1, KIAA0156, cyclophilin B, Lck, MUC-1, mutant HLA-A2, HA1, HA2, H-Y and LacZ.

37. The method according to claim 20, wherein the EDTA has a concentration of 0.02mM to 20 mM.

38. The method according to claim 20, wherein a liquid depth of the PBS containing EDTA is 2 to 5 mm.

39. A method for preparing adoptive immune cells comprising the following steps of:
(a) obtaining mammalian antigen-presenting associated cells;
(b) culturing the resulting cells from step (a) in a culture liquid contained in a culture vessel coated with PVMan; and
(c) detaching the cells from step (b) by shaking the culture vessel without treating the cells with an enzyme and without using a cell detaching tool,
wherein the culture liquid in the step (b) contains PMA and cancer cell lysate.

* * * * *